United States Patent
Duncan et al.

(10) Patent No.: US 11,782,020 B2
(45) Date of Patent: Oct. 10, 2023

(54) ADJUSTMENT OF A PH ELECTRODE CARBON REGION

(71) Applicants: Hach Lange GmbH, Berlin (DE); University of Warwick, Coventry (GB)

(72) Inventors: Zoë Duncan, Daventry (GB); Joshua James Tully, Coventry (GB)

(73) Assignees: HACH LANGE GMBH, Berlin (DE); UNIVERSITY OF WARWICK, Coventry (GB)

( * ) Notice: Subject to any disclaimer, the term of this patent is extended or adjusted under 35 U.S.C. 154(b) by 96 days.

(21) Appl. No.: 17/126,617

(22) Filed: Dec. 18, 2020

(65) Prior Publication Data

US 2021/0333234 A1 Oct. 28, 2021

Related U.S. Application Data

(60) Provisional application No. 63/016,708, filed on Apr. 28, 2020.

(51) Int. Cl.
  *C01B 32/28* (2017.01)
  *G01N 27/30* (2006.01)
  *C25B 11/043* (2021.01)
  *G01N 27/416* (2006.01)
  *G01N 33/18* (2006.01)

(52) U.S. Cl.
  CPC ......... *G01N 27/4165* (2013.01); *C01B 32/28* (2017.08); *C25B 11/043* (2021.01); *G01N 27/302* (2013.01); *G01N 27/308* (2013.01); *G01N 33/18* (2013.01)

(58) Field of Classification Search
  CPC ............... G01N 27/302; G01N 27/308; G01N 27/4165; C25B 11/043; C01B 32/28
  See application file for complete search history.

(56) References Cited

U.S. PATENT DOCUMENTS

| | | | |
|---|---|---|---|
| 9,618,495 | B2 | 4/2017 | Rajasekharan |
| 11,029,280 | B2 | 6/2021 | Kroll et al. |
| 11,169,112 | B2 | 11/2021 | Rajasekharan et al. |
| 11,209,379 | B2 | 12/2021 | Hutton et al. |

(Continued)

OTHER PUBLICATIONS

J. Ryl, et al., Study on surface termination of boron-doped diamond electrodes under anodic polarization in H2SO4 by means of dynamic impedance technique, Carbon, 2016(92), p. 1093-1105. (Year: 2016).*

(Continued)

*Primary Examiner* — Caitlyn Mingyun Sun
(74) *Attorney, Agent, or Firm* — Ference & Associates LLC

(57) ABSTRACT

An embodiment provides a method for modifying a carbon region on a boron-doped diamond electrode surface, comprising: placing a boron-doped diamond electrode surface in an aqueous solution, wherein the aqueous solution comprises an ionic treatment solution; applying a voltage difference across the boron-doped diamond electrode surface; and modifying a carbon region on an area of the boron-doped diamond electrode surface, wherein the modifying is responsive to application of the voltage while the boron-doped diamond electrode surface is in the aqueous solution, wherein the modification continues until a desired signal of the carbon region is reached. Other aspects are described and claimed.

10 Claims, 4 Drawing Sheets

(56) References Cited

U.S. PATENT DOCUMENTS

| | | | |
|---|---|---|---|
| 11,249,042 | B2 | 2/2022 | Macpherson et al. |
| 2017/0322172 | A1* | 11/2017 | Hutton ................ G01N 27/302 |
| 2019/0369045 | A1 | 12/2019 | Rajasekharan et al. |
| 2020/0400610 | A1 | 12/2020 | Rajasekharan et al. |
| 2021/0003529 | A1 | 1/2021 | Duncan et al. |
| 2021/0252644 | A1 | 8/2021 | Duncan |
| 2021/0333231 | A1 | 10/2021 | Duncan et al. |
| 2022/0196588 | A1 | 6/2022 | Salzer |

OTHER PUBLICATIONS

C.H. Goeting, Electrochemically induced surface modifications of boron-doped diamond electrodes: an X-ray photoelectron spectroscopy study, Diamond and Related Materials, 2000 (9), p. 390-96. (Year: 2000).*

J.V. Macpherson, A practical guide to using boron doped diamond in e3lectrochemical research, Phys. Chem. Chem. Phys. 2015 (17), p. 2935-49. (Year: 2015).*

Ayres Zoe J et al: "Impact of chemical vapour deposition plasma inhomogeneity on the spatial variation of sp2carbon in boron doped diamond electrodes", Carbon, Elsevier Oxford, GB, vol. 121, Jun. 3, 2017 (Jun. 3, 2017), pp. 434-442.

Hutton L et Al: "Amperometric oxygen ensor based on a platinum nanoparticle-modified polycrystalline boron doped diamond disk electrode", Analytical Chemistry, American Chemical Society, US, vol. 81, No. 3, Feb. 1, 2009 (Feb. 1, 2009), pp. 1023-1032.

Mahe E et al: "Electrochemical reactivity at graphitic microdomains on polycrystalline boron doped diamond thin-films electrodes", Electrochimica Acta, Els Ev I Er, Amsterdam, NL, vol. 50, No. 11, Nov. 23, 2004 (Nov. 23, 2004), pp. 2263-2277.

"Baluchova Simona et al:", "Recent progress in the applications of boron doped diamond electrodes in electroanalysis of organic compounds and biomolecules—A review", Analytica Chimica Acta, Elsevier, Amsterdam, NL, vol. 1077, May 22, 2019 (May 22, 2019), pp. 30-66.

"Oliveira S C B et al:", "Voltammetric and electrochemical impedance spectroscopy characterization of a cathodic and anodic pretreated boron doped diamond electrode", Electrochimica Acta, Elsevier, Amsterdam, NL, vol. 55, No. 15, Mar. 16, 2010 (Mar. 16, 2010), pp. 4599-4605.

* cited by examiner

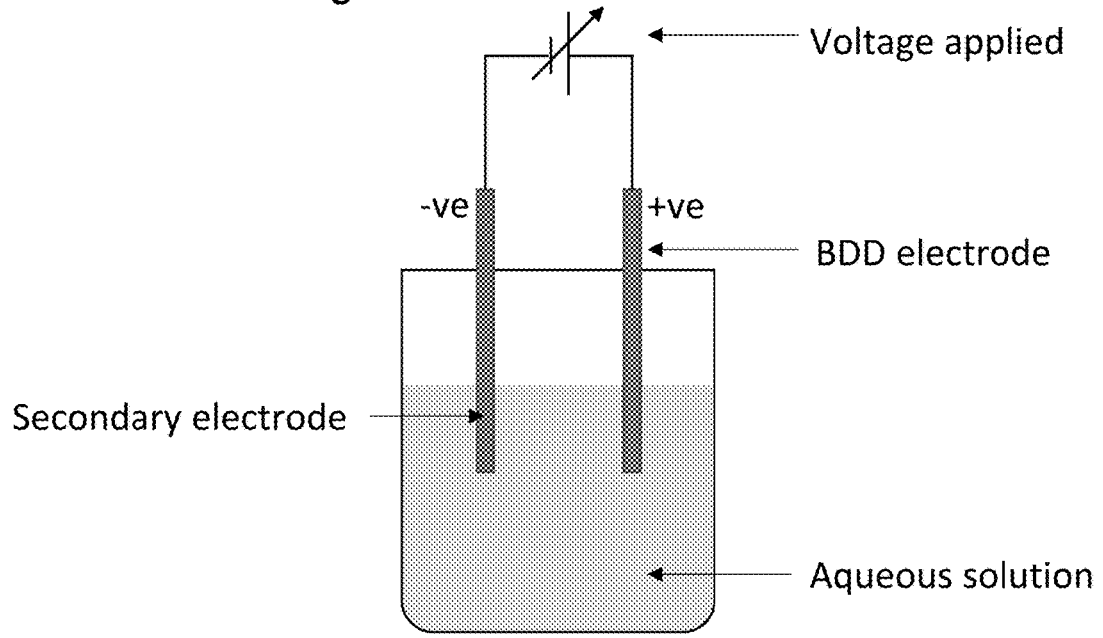
FIG 1A. Contact arrangement
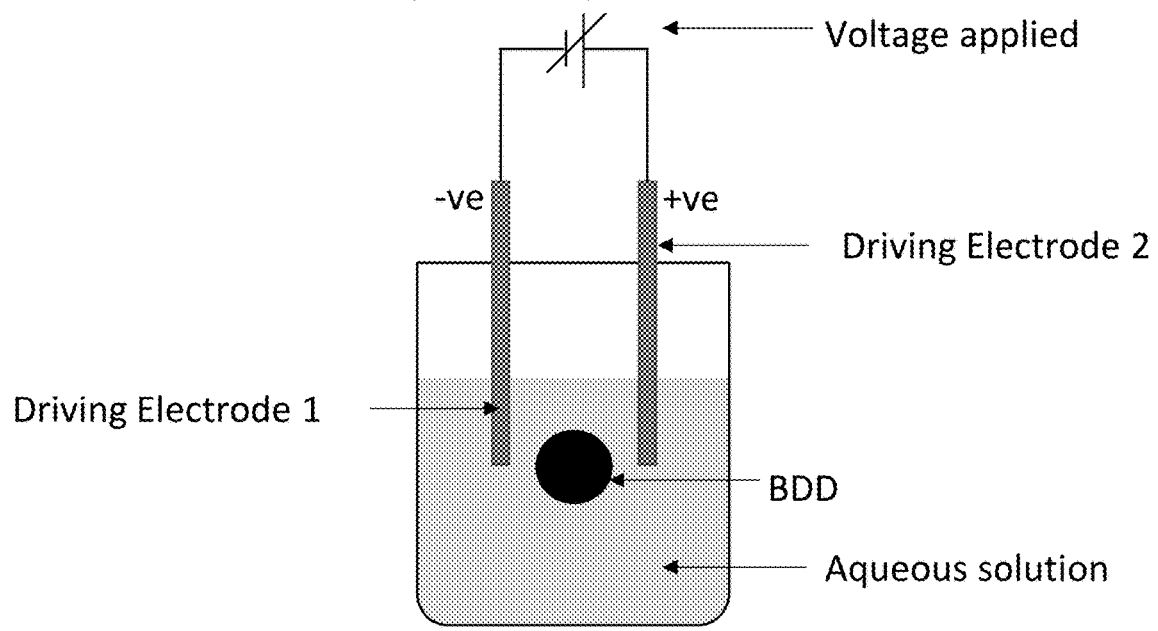
FIG.1B. Non-contact arrangement/bipolar

ADJUSTMENT OF A PH ELECTRODE CARBON REGION

CROSS REFERENCE TO RELATED APPLICATION

This application claims priority to U.S. Provisional Patent Application Ser. No. 63/016,708, filed on Apr. 28, 2020, and entitled "ADJUSTMENT OF A pH ELECTRODE CARBON REGION," the contents of which are incorporated by reference herein.

FIELD

This application relates generally to pH measurement of an aqueous sample, and, more particularly, to pH electrodes with a carbon region.

BACKGROUND

Ensuring water quality is critical to the health and well-being of humans, animals, and plants, which are reliant on water for survival. One parameter of water that may be measured is the pH. The measurement of pH of an aqueous sample is critical in a number of industries such as pharmaceuticals, biomedical, water supply, and other manufacturing fields. Measurement of pH may allow for proper treatment of water or ensuring proper water quality for sensitive purposes, and allows for identifying the overall quality of the water. One method to measure pH in an aqueous sample includes the use of electrodes which require constant maintenance and calibration of the pH measurement system.

BRIEF SUMMARY

In summary, one embodiment provides a method for modifying a carbon region on a boron-doped diamond electrode surface, comprising: placing a boron-doped diamond electrode surface in an aqueous solution, wherein the aqueous solution comprises an ionic treatment solution; applying a voltage difference across the boron-doped diamond electrode surface; and modifying a carbon region on an area of the boron-doped diamond electrode surface, wherein the modifying is responsive to application of the voltage while the boron-doped diamond electrode surface is in the aqueous solution, wherein the modification continues until a desired signal of the carbon region is reached.

Another embodiment provides a device for modifying a carbon region on a boron-doped diamond electrode surface, comprising: a boron-doped diamond electrode surface; at least one other electrode; an aqueous solution; a voltage generator; a processor; a memory device that stores instructions executable by the processor to: place a boron-doped diamond electrode surface in an aqueous solution, wherein the aqueous solution comprises an ionic treatment solution; apply a voltage difference across the boron-doped diamond electrode surface; and modify a carbon region on an area of the boron-doped diamond electrode surface, wherein the modifying is responsive to application of the voltage while the boron-doped diamond electrode surface is in the aqueous solution, wherein the modification continues until a desired signal of the carbon region is reached.

A further embodiment provides a system for modifying a carbon region on a boron-doped diamond electrode surface, comprising: a volume of aqueous solution; a voltage generator; a boron-doped diamond electrode surface; and a storage device having code stored therewith, the code being executable by the processor and comprising: code that places a boron-doped diamond electrode surface in an aqueous solution, wherein the aqueous solution comprises an ionic treatment solution; code that applies a voltage difference across the boron-doped diamond electrode surface; and code that modifies a carbon region on an area of the boron-doped diamond electrode surface, wherein the modifying is responsive to application of the voltage while the boron-doped diamond electrode surface is in the aqueous solution, wherein the modification continues until a desired signal of the carbon region is reached.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 1A illustrates a schematic diagram of adjustment of a pH electrode carbon region in an example contact arrangement embodiment. FIG. 1B illustrates a schematic diagram of adjustment of a pH electrode carbon region in an example non-contact arrangement embodiment.

DETAILED DESCRIPTION

Figure 2:
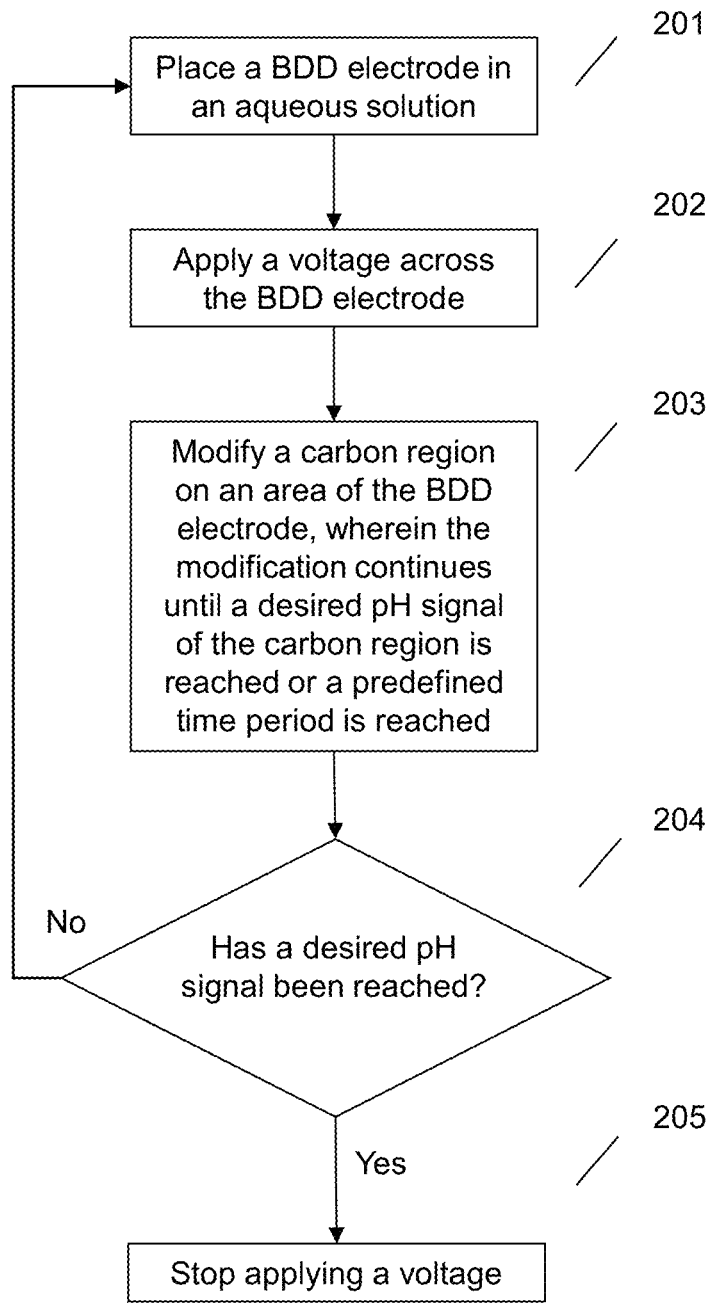
FIG. 2 illustrates a flow diagram of adjustment of a pH electrode carbon region in an example embodiment.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The measurement of the pH of water or other aqueous solutions or samples is common and allows for determination of the quality or other characteristics of the aqueous solution. Conventional pH electrodes for measurement of pH may be constructed using fragile, thin glass. This glass breaks easily leading to higher replacement and maintenance costs. The possible breakage of glass pH electrodes may also limit their use in food and beverage applications. Conventional pH electrodes also may have "alkali errors." These errors arise from interfering ions such as sodium and potassium affecting the pH response at high pH values. A commercial need exists for a robust pH measurement electrode that requires less maintenance while maintaining measurement of pH in sample containing heavy metals or a low conductivity sample, especially in an unbuffered, aqueous sample.

Another method of measuring pH of an aqueous sample uses a laser machined boron-doped diamond material to create an electrode sensor capable of measuring pH. Laser machining of the boron-doped diamond creates pH sensitive quinone-like structures on the boron-doped diamond material, due to the introduction of $sp^2$ carbon. These laser machined areas or pits may constitute a single spot (See U.S. patent application Ser. No. 16/459,300) or be in an array pattern. In other words, the laser machined areas may be a series of spots across a surface. The laser machining of these multiple spots may be challenging. For example, an array of laser machines pits across a surface requires using the laser repeatedly across the surface.

A boron-doped diamond pH electrode may give greater accuracy, especially improved accuracy in samples with low conductivity or low buffer capacity. boron-doped diamond pH electrodes may measure pH in all pH ranges including an environmentally relevant range of pH 4 to 11. Better control over quinone-like structure is required as the quinone-like structure density and nature may impact accuracy in low conductive and low buffer capacity solutions. What is needed is a method and system to adjust the carbon region or $sp^2$ carbon region upon a boron-doped diamond pH electrode.

Accordingly, the systems and methods as described herein may be used to adjust or tune an $sp^2$ carbon region of a boron-doped diamond electrode. Reference to electrode throughout refers to a boron-doped diamond surface, which may be packaged into electrode format or left in wafer format. The boron-doped diamond electrode may be placed in an aqueous solution. The boron-doped diamond electrode may have a carbon region or $sp^2$ carbon. The carbon region may be laser machined upon the boron-doped diamond surface. The laser machining may occur before the adjustment of the boron-doped diamond. In an embodiment, a voltage may be passed through the boron-doped diamond in an electrode format (contact method), or through a non-contact method such as a bipolar arrangement, where boron-doped diamond material (or wafer) is placed in the aqueous solution. In an embodiment, the system and method may adjust or tune a $sp^2$ component of the boron-doped diamond surface. The modification of the $sp^2$ diamond material may be performed using the contact or non-contact method. The adjustment may reduce or modify overall quinone-like structures and/or their density. For clarity, the term modification may be used for adjustment, removal, tuning, or the like, the quinone-like structures and/or the density of the quinone structures on the boron-doped diamond surface. This may be in a boron-doped diamond pH electrode format. The reduction or modification of quinone-like structure/density may improve overall unbuffered pH performance. In an embodiment, the system and method may apply a voltage across boron-doped diamond electrode until a desired result is achieved. The system and method may monitor a pH signal or a peak in current from the electrode undergoing adjustment. The adjusted electrode may determine a pH by identifying an electrical potential of an aqueous sample, or may be used to measure an electrochemical component of a sample.

The electrode may have a carbon region and a pH sensitive carbon region. For example, the electrode may be a boron-doped diamond electrode with a plurality of $sp^2$ carbon regions. The pH sensitive carbon region may be laser machined. The laser micromachined electrode surface may comprise $sp^2$ carbon, as well as $sp^3$ carbon(diamond)-doped with elements like boron (boron-doped diamond). The pH sensitive carbon region may be a $sp^2$ carbon region that is included on a boron doped diamond-based pH electrode. Being included may mean that the $sp^2$ carbon region is introduced into, integrated into, contained within, laser micro machined into, or otherwise integrated into the boron doped diamond surface. In other words, while the $sp^2$ carbon region and the boron doped diamond are integrated into the same electrode, they are chemically different regions of the electrode. The $sp^2$ carbon region may have oxidized carbon structures. The oxidized carbon structure may have quinone or quinone-like groups. The system and method described herein may provide an adjustment of the quinone, or quinone-like group density of the $sp^2$ region of the boron-doped diamond electrode.

The use of boron-doped diamond serves as a better electrode material than other carbon-based or metallic materials (e.g., silver, gold, mercury, nickel, etc.) because these materials may be more electrocatalytically active, and may generate interfering signals contributing to the errors in the measurement of pH.

The illustrated example embodiments will be best understood by reference to the figures. The following description is intended only by way of example, and simply illustrates certain example embodiments.

Referring now to FIG. 1A-B, an embodiment may modify the quinone-like density of a boron-doped diamond electrode. For example, FIG. 1A illustrates a contact arrangement. In a contact arrangement, a boron-doped diamond electrode may be electrically coupled and in an aqueous solution. For example, a $sp^2$ carbon region with quinone-like groups may be laser machined on a boron-doped diamond electrode. The laser machining may occur prior to an adjustment or tuning of the pH boron-doped diamond electrode. In an embodiment, the boron-doped diamond electrode may be placed in a volume of aqueous solution. In an embodiment, a voltage may be applied across the boron-doped diamond electrode within the aqueous solution. In an embodiment, there may be a plurality of boron-doped diamond electrodes in a volume of aqueous solution. The voltage may be applied until a desired density of quinone-like structures remain on the boron-doped diamond electrode. In an embodiment, the boron-doped diamond electrode used in a final application may be connected at the cathode or the anode. In an embodiment, the opposite pole may be a boron-doped diamond electrode, or an electrode made of a different material. In this manner, a pole selected for the boron-doped diamond electrode may have an effect on the modification of an electrode based on either a cathode or an anode position. In an embodiment, the length of time a voltage is applied or the amplitude of the voltage may be determined by measuring a pH peak or other current peak from the boron-doped diamond electrode in the bath of aqueous solution, or taking the electrode out at regular time intervals and checking the response in another solution. In other words, an electrode may be removed from a solution for modification and placed in another solution to check electrode performance. As another example, FIG. 1B illustrates a non-contact or bipolar arrangement. In a non-contact arrangement, the boron-doped diamond may be in the aqueous solution. In other words, a non-contact arrangement involves the placement of a boron-doped diamond sample or wafer between the driving electrodes, where a voltage is applied directly to the driving electrodes, not the boron-doped diamond. A non-contact or bipolar arrangement, is where the boron-doped diamond electrode or wafer to be treated is placed between two driving electrodes generating possible oxidizing species required for the removal/modification to occur. The boron-doped diamond sample or wafer may then be placed in electrode format after non-contact treatment, to create a boron-doped diamond pH electrode.

The boron-doped diamond electrode may measure pH of a sample. In an embodiment, an electrode may be laser micromachined or machined to introduce an array of pits into the electrode surface or face. In an embodiment, a combination of pits may create a pattern upon the electrode. The laser machining may introduce $sp^2$ carbon upon the electrode. The $sp^2$ carbon may include quinone or quinone-like groups which may undergo proton-coupled electron transfer. In an embodiment, the laser machined electrodes may be used to perform electrochemical measurements to measure a pH response on the electrode in which the observed current-voltage peak may be indicative of a pH of a sample. In an embodiment, the aqueous solution and/or the applied voltage may remove quinone-like structures from the boron-doped diamond electrode. The system and method may remove, etch, or adjust $sp^2$ carbon and modify the surface termination including the associated oxygen containing functional groups over time. In an embodiment, the time of applied voltage, the voltage amplitude, type of aqueous solution, salt concentration of aqueous solution, or the like may be altered to achieve a desire result. The adjustment may be performed manually, controlled by a system, and/or be fully automated.

In an embodiment, a boron-doped diamond pH electrode may operate in a Nernstian manner across a pH range in a buffered solution. Such properties may be present in a boron-doped diamond electrode before or after adjustment. In an unbuffered solution, a boron-doped diamond pH electrode may deviate from an expected theoretical response. A deviation may be linked to an amount of $sp^2$ carbon present and/or the amount of quinone-like groups on an electrode surface. Thus, control of carbon region and associated density of quinone-like structures may be critical to the efficient manufacture of an accurate electrode. The system and method disclosed may provide better manufacturing of a suitable boron-doped diamond pH electrode with $sp^2$ regions with quinone-like structures.

Referring to FIG. 2, an example embodiment to adjust a boron-doped diamond electrode with a carbon region is illustrated. At 201, in an embodiment, a boron-doped diamond electrode may be placed in an aqueous solution. The boron-doped diamond electrode may be placed into an aqueous solution either manually or in an automated manner. In an embodiment, there may be a plurality of boron-doped diamond electrodes in an aqueous solution bath or volume. Multiple boron-doped diamond electrodes may be used to complete a circuit through the aqueous solution or multiple boron-doped diamond electrodes may be adjusted at the same time in a volume of aqueous solution.

In an embodiment, the aqueous solution may be an acid, base or neutral solution. The aqueous solution may comprise a source of ions such as an acid, strong, acid, base, or neutral solution which may be buffered or unbuffered. The source of ions may be referred to an ionic treatment solution. It may be a strong or weak acid. The acid may be a concentrated acid solution. The acid may be greater than or equal to 0.01 M. The acid may be sulfuric acid, nitric acid, hydrochloric acid, citric acid, acetic acid or the like. It may be a base solution. The base may be greater than or equal to 0.01 M. The base may be potassium hydroxide, sodium hydroxide, ammonia, methylamine or the like. It may be a salt solution. The salt solution may be any pH, including neutral. The solution may be buffered or unbuffered. The salt solution may be potassium nitrate, potassium chloride, potassium sulphate, or the like. An aqueous solution composition, concentration, and length of time in the aqueous solution may be selected based upon the application for which the boron-doped diamond pH electrode is adjusted for use. The aqueous solution components, as well as an applied voltage, may modify $sp^2$ carbon from the boron-doped diamond electrode.

At 202, in an embodiment, a voltage may be applied across the boron-doped diamond electrode in the aqueous solution volume. In an embodiment, the voltage may be equal to or greater than 5 volts with respect to ground. In an embodiment, the voltage difference applied may be equal to, around, or greater than 30 volts with respect to ground. In an embodiment, the voltage time, duration, or the like may be altered. The system and method may follow preprogrammed instructions, input parameters from a user or database, or the like. The voltage may be applied using a voltage generator. The voltage may be applied across the boron-doped diamond electrode selected for tuning, across the aqueous solution volume, and/or another electrode within the aqueous solution volume to complete the circuit. The other electrode may be another boron-doped diamond electrode, another type of electrode, or any conductive material.

At 203, in an embodiment, a carbon region of a boron-doped diamond electrode may be removed. In an embodiment, the removal/modification of a pH active carbon region may be referred to as adjusting, tuning, or etching the carbon region. This carbon region may be pH sensitive. In an embodiment, the electrochemistry of the method and system may allow a generation of radical species such as sulfates, hydroxyl, nitrates, or the like, dependent on the aqueous solution used, near or around the electrode surface. The radical species may assist in the removal/modification of $sp^2$ at the boron-doped diamond electrode. Additionally, or alternatively, localized heating at the electrode surface may assist in $sp^2$ removal/modification.

In an embodiment, a higher quinone surface coverage of a boron-doped diamond electrode may lead to increased pH errors in unbuffered, aqueous solutions. The system and method herein may provide a systemic removal/modification of quinone-like groups. The removal/modification of quinone-like groups may improve boron-doped diamond pH electrode performance. The increase in boron-doped diamond pH electrode performance may allow for a more accurate pH measurement in unbuffered conditions. In other words, the $sp^2$ component may be tuned or adjusted to ensure some of the quinone-like groups remain, as these quinone-like groups may detect a pH signal.

Figure 3:
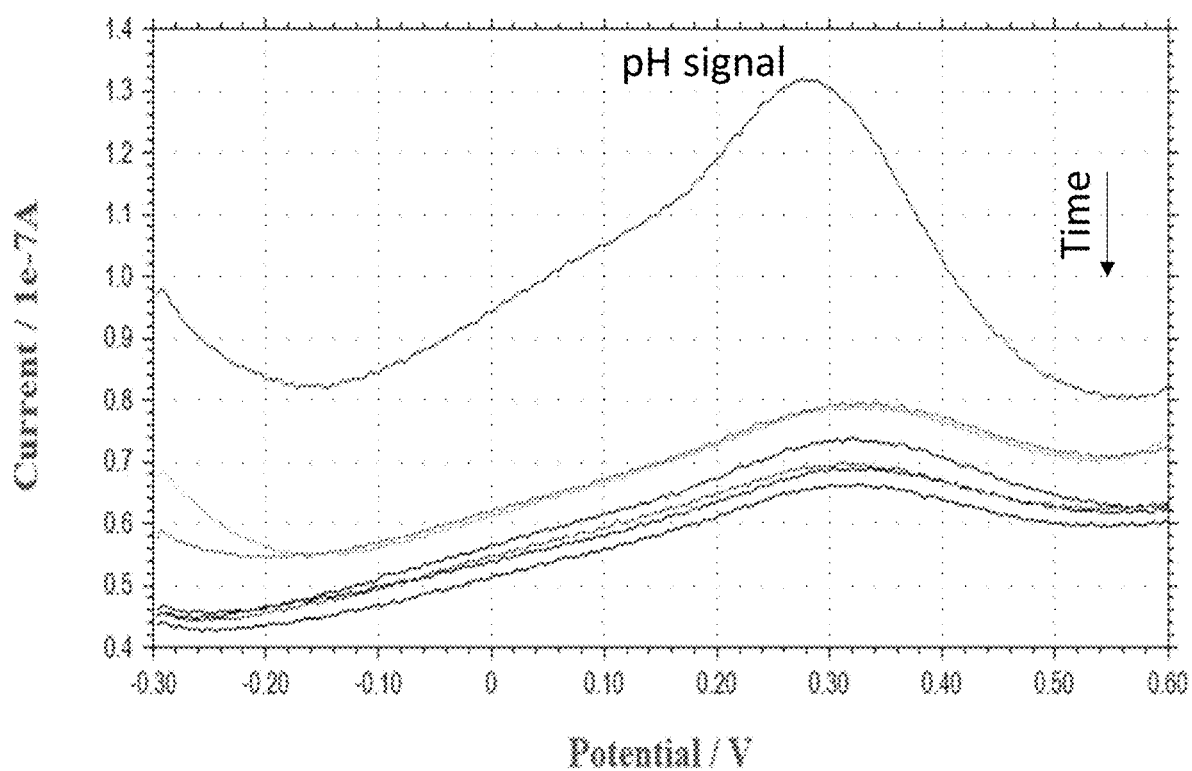
FIG. 3 illustrates a current-voltage relationship over time of a pH electrode carbon region in an example embodiment.

At 204, the system and method may determine if a desired pH signal has been detected. In an embodiment, the system and method may use a technique as illustrated in FIG. 3. for determination. For example, a voltage may be applied until a peak current of a desired amplitude or a pH signal is measured. An example of such method illustrated in FIG. 3 of a current-voltage relationship over time of an adjustment of a pH boron-doped diamond electrode. In other words, as voltage is applied to a boron-doped diamond electrode in an ionic treatment solution over time, the pH sensitive $sp^2$ region may be modified, and the pH signal may also be reduced. In an embodiment, a peak of the current-voltage relationship may correlate to a pH value. In an embodiment, a rate of removal/modification of $sp^2$ carbon may be determined. The rate of removal/modification may be determined by measuring a pH signal over time during a boron-doped diamond electrode adjustment. The rate of removal/modification may be controlled by the system. In other words, the system may use a rate to determine the efficacy of the removal/modification process.

If the system determines a desired pH signal has not been reached, the system may continue to apply a voltage across the boron-doped diamond electrode being adjusted within the aqueous solution volume. In an embodiment, the method and system may adjust an amplitude, duration, and/or waveform to achieve a desired pH signal. In other words, the system may adjust voltage parameters to achieve a desired pH signal. However, if, at 204 a desired pH signal has been reached, the system may stop applying voltage at 205.

Measurement of a pH signal may be at periodic intervals set by the user or preprogrammed frequencies in the system. A measurement of the pH signal may be an output upon a device in the form of a display, printing, storage, audio, haptic feedback, or the like. Alternatively, or additionally, the output may be sent to another device through wired, wireless, fiber optic, Bluetooth®, near field communication, or the like. An embodiment may use an alarm to warn of a measurement outside acceptable or desired levels. An embodiment may use a system to shut down a voltage or alter a voltage within unacceptable parameters, limits, or thresholds. For example, a measuring device may be operatively coupled to a voltage generator.

In an embodiment, the system may detect when a volume of aqueous solution becomes diluted, low on volume, depleted, or the like. For example, the system may receive an alert of a volume of aqueous solution outside of specification and provide an alert or take action to flush or replenish the volume of aqueous solution. Additionally or alternatively, the system may output an alarm, log an event, or the like.

In an embodiment, the performance of the method and system of the adjustment of a boron-doped diamond electrode may be communicated and/or stored. The system may connect to a communication network. The system may alert a user or a network. This alert may occur whether a boron-doped diamond electrode is adjusted properly or improperly. An alert may be in a form of audio, visual, data, storing the data to a memory device, sending the output through a connected or wireless system, printing the output or the like. The system may log information such as the measurement location, a corrective action, geographical location, time, date, number of measurement/adjustment cycles, pH signal, current-voltage plots, or the like. The alert or log may be automated, meaning the system may automatically output whether a correction was required or not. The system may also have associated alarms, limits, or predetermined thresholds. For example, if a boron-doped diamond electrode adjustment falls below a threshold or limit. Alarms or logs may be analyzed in real-time, stored for later use, or any combination thereof.

In an embodiment, the electrodes may be fully or at least partially disposed in the aqueous solution volume. For example, if the aqueous solution is introduced into a chamber having one or more electrodes, the aqueous solution may at least partially cover the one or more electrodes. As another example, the one or more electrodes may be partially disposed within the chamber and/or aqueous solution with the other portion of the electrode outside the chamber and/or aqueous solution. Thus, when the aqueous solution is introduced into the chamber it may only cover the portion of the electrodes that are within the chamber. The aqueous solution may be in a chamber, beaker, or any vessel of a material suitable for aqueous solution.

The various embodiments described herein thus represent a technical improvement to conventional methods, such as high temperature acid cleaning, providing more precise control over the modification process for adjusting a pH sensitive boron-doped diamond electrode. Using the techniques as described herein, an embodiment may use a method and system for an adjusting $sp^2$ carbon regions and/or quinone-like density on a boron-doped diamond electrode. This is in contrast to conventional methods with limitations mentioned above. Such techniques provide a better method to construct an instrument for pH measurement.

Figure 4:
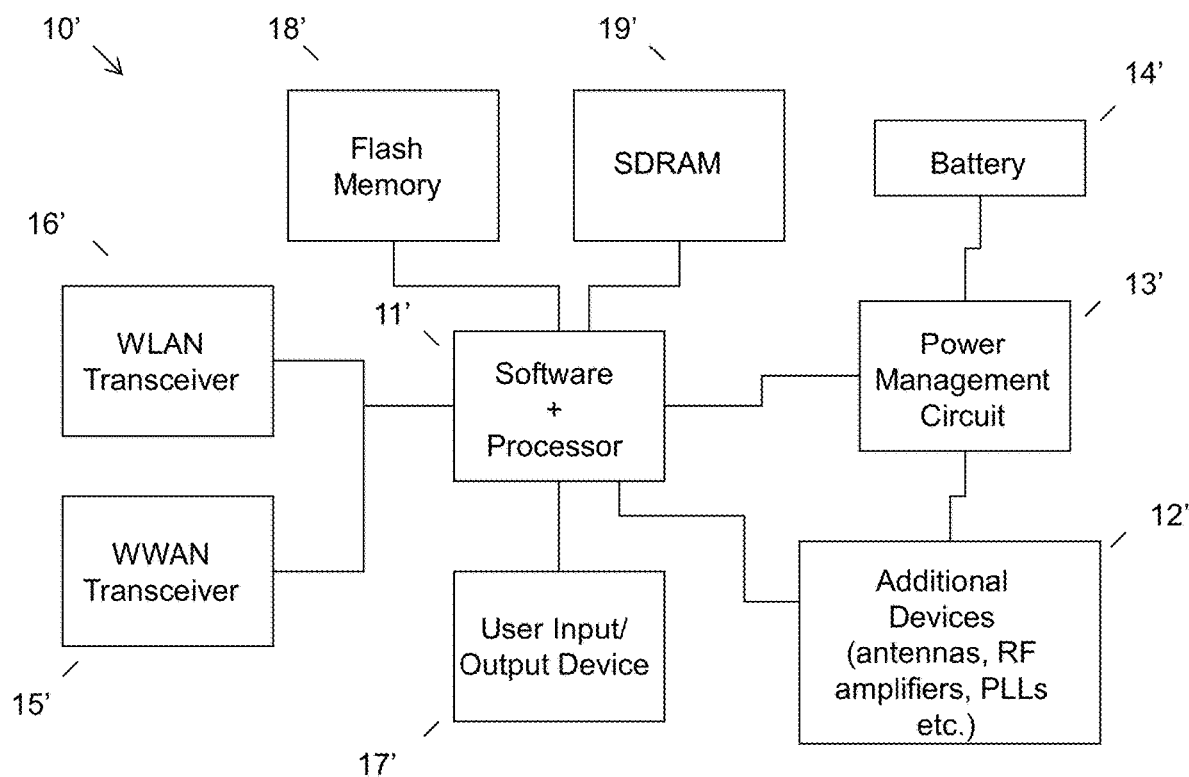
FIG. 4 illustrates an example of computer circuitry.

While various other circuits, circuitry or components may be utilized in information handling devices, with regard to an instrument for adjustment of a pH electrode carbon region according to any one of the various embodiments described herein, an example is illustrated in FIG. 4. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment of an instrument for adjustment of a pH electrode carbon region.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a measurement device such as illustrated in FIG. 1A-B, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated. Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for modifying a carbon region on a boron-doped diamond electrode surface, comprising:
    placing the boron-doped diamond electrode surface in an aqueous solution, wherein the aqueous solution comprises an ionic treatment solution;
    applying a voltage difference between two driving electrodes and across the boron-doped diamond electrode surface, wherein the voltage difference is applied directly to the two driving electrodes, wherein the boron-doped diamond electrode surface is placed between the two driving electrodes in a non-contact arrangement without contacting the two driving electrodes; and
    modifying the carbon region on an area of the boron-doped diamond electrode surface, wherein the modifying is responsive to application of the voltage difference while the boron-doped diamond electrode surface is in the aqueous solution, wherein the modification continues until a desired signal of the carbon region is reached.

2. The method of claim 1, wherein the ionic treatment solution comprises ions and is selected from the group consisting of: sulfuric acid, nitric acid, hydrochloric acid, citric acid, acetic acid, potassium hydroxide, sodium hydroxide, ammonia, methylamine, potassium nitrate, potassium sulfate, and potassium chloride.

3. The method of claim 1, wherein the carbon region is a sp2 carbon region.

4. The method of claim 1, wherein the modifying alters at least one of: oxidized carbon structures and quinone-like groups.

5. The method of claim 1, wherein the voltage difference applied is equal to or greater than 5V as measured against ground.

6. The method of claim 1, wherein the applied voltage difference generates radical species.

7. The method of claim 1, further comprising measuring a current-voltage relationship of the carbon region during modification, wherein the measuring is performed for a duration until a predetermined modification completes.

8. The method of claim 7, wherein a measured current at a predetermined applied voltage decreases with modification of the carbon region.

9. The method of claim 7, wherein a peak of the current-voltage relationship correlates to a pH value.

10. The method of claim 9, further comprising determining the peak of the current-voltage relationship matches a peak of a desired pH signal.

* * * * *